United States Patent
Stender et al.

(10) Patent No.: US 8,206,921 B2
(45) Date of Patent: Jun. 26, 2012

(54) **DETECTION OF METHICILLIN-RESISTANT *STAPHYLOCOCCUS AUREUS***

(75) Inventors: Henrik Stender, Gentofte (DK); Anne Karin Ildor Rasmussen, Taastrup (DK); Mark J. Fiandaca, Princeton, MA (US)

(73) Assignee: AdvanDx, Inc., Woburn, MA (US)

( * ) Notice: Subject to any disclaimer, the term of this patent is extended or adjusted under 35 U.S.C. 154(b) by 23 days.

(21) Appl. No.: 12/620,187

(22) Filed: Nov. 17, 2009

(65) Prior Publication Data

US 2010/0143923 A1 Jun. 10, 2010

Related U.S. Application Data

(63) Continuation of application No. PCT/US2008/006285, filed on May 16, 2008.

(60) Provisional application No. 60/930,840, filed on May 18, 2007.

(51) Int. Cl.
 *C12Q 1/68* (2006.01)
 *C12P 19/34* (2006.01)

(52) U.S. Cl. ..................... 435/6.11; 435/91.2

(58) Field of Classification Search ............ None
See application file for complete search history.

(56) References Cited

U.S. PATENT DOCUMENTS

| | | | |
|---|---|---|---|
| 2003/0124521 A1* | 7/2003 | Coull et al. | 435/6 |
| 2005/0032091 A1* | 2/2005 | Stender et al. | 435/6 |
| 2005/0272078 A1 | 12/2005 | Fiandaca et al. | |
| 2006/0057613 A1 | 3/2006 | Ramakrishnan et al. | |

FOREIGN PATENT DOCUMENTS

| | | | |
|---|---|---|---|
| EP | 1 529 847 A | | 5/2005 |
| WO | WO 02/099034 A | | 12/2002 |
| WO | WO 2006/116010 A | | 11/2006 |
| WO | WO 2007/058939 A | | 5/2007 |
| WO | WO 2007/133732 A | | 11/2007 |
| WO | WO 2008/143972 A2 | | 11/2008 |

OTHER PUBLICATIONS

Database Geneseq [online] Jun. 22, 1999, "Sequence 2 Provided in Fig 18 of JP11056371," retrieved from EBI accession No. GSN:AAX32460.
Database EMBL [online] Sep. 30, 2005, "*Staphylococcus warneri* Strain 8-80 OrfX (orfX) Gene, Partial cds," retrieved from EBI accession No. EMBL:AY751832.
Notification of Transmittal of the International Search Report and the Written Opinion of the International Searching Authority, or the Declaration, International Search Report and Written Opinion, from International Application No. PCT/US2008/006285, 23 pages, dated Feb. 4, 2009.
Notification Concerning Transmittal of International Preliminary Report on Patentability and International Preliminary Report on Patentability from International Application No. PCT/US2008/006285, 13 pages, dated Dec. 3, 2009.

* cited by examiner

*Primary Examiner* — Katherine Salmon
(74) *Attorney, Agent, or Firm* — Hamilton, Brook, Smith & Reynolds, P.C.

(57) ABSTRACT

This invention relates to the use of genetic probes for detection of the presence of the SCCmec cassette in *Staphylococcus aureus*. In one aspect, the invention allows specific detection and identification of methicillin-resistant *S. aureus* (MRSA) in a clinical sample without interference from the presence of other non-*S. aureus* methicillin-resistant staphylococci. In another aspect, the invention allows specific detection and identification of methicillin-resistant coagulase negative staphylococci (MRCNS) originating from a clinical sample without interference from the presence of methicillin-resistant *S. aureus*.

3 Claims, No Drawings

SEQUENCE LISTING

<160> NUMBER OF SEQ ID NOS: 36

<210> SEQ ID NO 1
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 1
aatccttcgg aagatagcat ctttccttgt atttctaatg         40

<210> SEQ ID NO 2
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 2
gctattattt acttgaaatg aaagactgcg gaggctaact         40

<210> SEQ ID NO 3
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 3
taatccaata tttcatatat gtaattcctc cacatctcat         40

<210> SEQ ID NO 4
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 4
actttagtca aatcatcttc actagtgtaa ttatcgaatg         40

<210> SEQ ID NO 5
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 5
tgttcaatta acacaacccg catcatttga tgtgggaatg         40

<210> SEQ ID NO 6
<211> LENGTH: 44
<212> TYPE: DNA
<213> ORGANISM: Artificial Sequence
<220> FEATURE:
<223> OTHER INFORMATION: oligonucleotide probe

<400> SEQUENCE: 6
taataaactc tgctttatat tataaaatta cggctgaaat aacc         44

<210> SEQ ID NO 7
<211> LENGTH: 45
<212> TYPE: DNA

```
<213> ORGANISM: Artificial Sequence
<220> FEATURE:
<223> OTHER INFORMATION: oligonucleotide probe

<400> SEQUENCE: 7
tgttttcttc aaatattatc tcgtaattta ccttgttcat taaac                    45

<210> SEQ ID NO 8
<211> LENGTH: 43
<212> TYPE: DNA
<213> ORGANISM: Artificial Sequence
<220> FEATURE:
<223> OTHER INFORMATION: oligonucleotide probe

<400> SEQUENCE: 8
tttattcttc aaagatttga gctaatttaa taattttctc ata                      43

<210> SEQ ID NO 9
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 9
aattaatctg attttcactc ttcatctact tactcatatt                          40

<210> SEQ ID NO 10
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 10
aacataacag caattcacat aaacctcata tgttctgata                          40

<210> SEQ ID NO 11
<211> LENGTH: 9
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_difference
<222> LOCATION: (2)...(8)
<223> OTHER INFORMATION: locked nucleic acid

<400> SEQUENCE: 11 gaggctaac                                                             9

<210> SEQ ID NO 12
<211> LENGTH: 9
<212> TYPE: DNA
<213> ORGANISM: Artificial Sequence
<220> FEATURE:
<223> OTHER INFORMATION: oligonucleotide probe

<400> SEQUENCE: 12 gaggctaac                                                             9

<210> SEQ ID NO 13
<211> LENGTH: 9
<212> TYPE: DNA
<213> ORGANISM: Artificial Sequence
<220> FEATURE:
<223> OTHER INFORMATION: oligonucleotide probe
<220> FEATURE:
```

```
<221> NAME/KEY: misc_difference
<222> LOCATION: (1)...(9)
<223> OTHER INFORMATION: peptide nucleic acid

<400> SEQUENCE: 13 ctgcggagg                                                                  9

<210> SEQ ID NO 14
<211> LENGTH: 29
<212> TYPE: DNA
<213> ORGANISM: Artificial Sequence
<220> FEATURE:
<223> OTHER INFORMATION: oligonucleotide probe

<400> SEQUENCE: 14
atttggtgtg ggaaggtcat cttgctgaa                                           29

<210> SEQ ID NO 15
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 15
tcgatatact tgttctatca acacgacgcg                                          30

<210> SEQ ID NO 16
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 16
tgttctatca acacgacgcg catcatttgg tgtgggaagg                               40

<210> SEQ ID NO 17
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 17
caaatacaaa gtcgctttgc ccttgtgtca                                          30

<210> SEQ ID NO 18
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 18
tttgaccttg tgtcatgcgt gtttgtagtt ctttagcgag                               40

<210> SEQ ID NO 19
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 19
tgtaaaccat tggagccacc tatgacaaat gtaaagtcgc                               40
```

```
<210> SEQ ID NO 20
<211> LENGTH: 9
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_difference
<222> LOCATION: (1)...(9)
<223> OTHER INFORMATION: locked nucleic acid

<400> SEQUENCE: 20 gaggctaac                                                                9

<210> SEQ ID NO 21
<211> LENGTH: 9
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_difference
<222> LOCATION: (2)...(8)
<223> OTHER INFORMATION: locked nucleic acid

<400> SEQUENCE: 21 ttcctccac                                                                9

<210> SEQ ID NO 22
<211> LENGTH: 9
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_difference
<222> LOCATION: (1)...(9)
<223> OTHER INFORMATION: locked nucleic acid

<400> SEQUENCE: 22 accattcac                                                                9

<210> SEQ ID NO 23
<211> LENGTH: 13
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_difference
<222> LOCATION: 2, 4, 6
<223> OTHER INFORMATION: locked nucleic acid

<400> SEQUENCE: 23
gcggaggcta act                                                          13

<210> SEQ ID NO 24
<211> LENGTH: 13
<212> TYPE: DNA
<213> ORGANISM: Artificial Sequence
<220> FEATURE:
<223> OTHER INFORMATION: oligonucleotide probe

<400> SEQUENCE: 24
gcggaggcta act                                                          13

<210> SEQ ID NO 25
<211> LENGTH: 16
<212> TYPE: DNA
```

<213> ORGANISM: Artificial Sequence
<220> FEATURE:
<223> OTHER INFORMATION: oligonucleotide probe
<220> FEATURE:
<221> NAME/KEY: misc_difference
<222> LOCATION: 2, 5, 8
<223> OTHER INFORMATION: locked nucleic acid

<400> SEQUENCE: 25
actgcggagg ctaact                                                         16

<210> SEQ ID NO 26
<211> LENGTH: 14
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_difference
<222> LOCATION: 1, 4, 7
<223> OTHER INFORMATION: locked nucleic acid

<400> SEQUENCE: 26
ctgcggaggc taac                                                           14

<210> SEQ ID NO 27
<211> LENGTH: 11
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_difference
<222> LOCATION: 1, 2, 4
<223> OTHER INFORMATION: locked nucleic acid

<400> SEQUENCE: 27
cggaggctaa c                                                              11

<210> SEQ ID NO 28
<211> LENGTH: 11
<212> TYPE: DNA
<213> ORGANISM: Artificial Sequence
<220> FEATURE:
<223> OTHER INFORMATION: oligonucleotide probe

<400> SEQUENCE: 28
cggaggctaa c                                                              11

<210> SEQ ID NO 29
<211> LENGTH: 10
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_difference
<222> LOCATION: 1, 2, 4
<223> OTHER INFORMATION: locked nucleic acid

<400> SEQUENCE: 29
cggaggctaa                                                                10

<210> SEQ ID NO 30
<211> LENGTH: 10
<212> TYPE: DNA
<213> ORGANISM: Artificial Sequence
<220> FEATURE:
<223> OTHER INFORMATION: oligonucleotide probe

```
<400> SEQUENCE: 30
cggaggctaa                                                          10

<210> SEQ ID NO 31
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 31
cattagaaat acaaggaaag atgctatctt ccgaaggatt                         40

<210> SEQ ID NO 32
<211> LENGTH: 27
<212> TYPE: DNA
<213> ORGANISM: Artificial Sequence
<220> FEATURE:
<223> OTHER INFORMATION: oligonucleotide probe

<400> SEQUENCE: 32
cattcccaca tcaaatgatg cgggttg                                       27

<210> SEQ ID NO 33
<211> LENGTH: 14
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_difference
<222> LOCATION: 1, 2, 4, 6
<223> OTHER INFORMATION: locked nucleic acid

<400> SEQUENCE: 33
gggttgtgtt aatt                                                     14

<210> SEQ ID NO 34
<211> LENGTH: 14
<212> TYPE: DNA
<213> ORGANISM: Artificial Sequence
<220> FEATURE:
<223> OTHER INFORMATION: oligonucleotide probe

<400> SEQUENCE: 34
gggttgtgtt aatt                                                     14

<210> SEQ ID NO 35
<211> LENGTH: 12
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_difference
<222> LOCATION: 1, 2, 4, 6
<223> OTHER INFORMATION: locked nucleic acid

<400> SEQUENCE: 35
gggttgtgtt aa                                                       12

<210> SEQ ID NO 36
<211> LENGTH: 12
<212> TYPE: DNA
<213> ORGANISM: Artificial Sequence
<220> FEATURE:
<223> OTHER INFORMATION: oligonucleotide probe
```

-continued

```
<400> SEQUENCE: 36
gggttgtgtt aa                                              12
```

DETECTION OF METHICILLIN-RESISTANT *STAPHYLOCOCCUS AUREUS*

RELATED APPLICATIONS

This application is a continuation of International Application No. PCT/US2008/006285, which designated the United States and was filed on May 16, 2008, published in English, which claims the benefit of U.S. Provisional Application No. 60/930,840 filed on May 18, 2007. The entire teachings of the above applications are incorporated herein by reference.

BACKGROUND OF THE INVENTION

Methicillin-resistant *Staphylococcus aureus* (MRSA) strains contain a SCCmec cassette, which may contain the mecA gene whose gene product confers methicillin resistance. Specific detection of MRSA by the presence of the SCCmec cassette has been used in a number of publications and patents (U.S. Pat. No. 6,156,507, US 2005019893). These various methods all rely on the use of primer set(s) where one (or more) primers target the *S. aureus* chromosomal DNA (external to SCCmec) and the other one (or more) primers target the SCCmec cassettes near the chromosomal integration site. Due to the presence of multiple SCCmec (sub) types, more than one primer set is needed to detect all MRSAs. SCCmec cassettes are also found in other Staphylococcus species, commonly known as coagulase-negative staphylococci, including *S. epidermidis, S. hominis, S. haemolyticus* and others. Current methods therefore use primers directed specifically to *S. aureus* chromosomal DNA (non-cassette regions) to assess the species identification and to avoid confusion between SCCmec cassettes detected in *S. aureus* and those in other staphylococci.

In theory, this is a clear strategy for MRSA detection, however, in practice this concept produces both false positive and false negative results as has been reported (Drews, et. al., J. Clin. Microbiol. 44:3794, 2006; Desjardins, et. al., J. Clin. Microbiol. 44:1219, 2006, Bishop, et. al. J. Clin. Microbiol. 44:2904, 2006) and there is therefore a need for improved methods with higher sensitivity and specificity.

SUMMARY OF THE INVENTION

Oligonucleotides or oligonucleotide mimics as defined herein can be used in methods to detect MRSA and MRCNS and to distinguish MRSA from MRCNS. The oligonucleotides and oligonucleotide mimics are, in some embodiments, set forth in the tables herein, and comprise sequences SEQ ID NOs 1-36. The oligonucleotides and oligonucleotide mimics are generally referred to as probes, especially as used in hybridization methods, or as primers, especially as used in DNA amplification methods.

In one embodiment the invention is a method of testing a sample for the presence or absence of SCCmec cassette DNA present as an insertion in chromosomal DNA of *Staphylococcus aureus*. The method includes (a) hybridizing the sample, under appropriate conditions, to one or more capture probe(s) that hybridize to chromosomal DNA of *Staphylococcus aureus* external to SCCmec by at least partially complementary sequences, the capture probe(s) being optionally attached to a support, (b) hybridizing the sample to one or more detector probe(s) that hybridize to SCCmec cassette DNA by at least partially complementary sequences, and (c) detecting each of the detector probe(s), which may include application of means of detection appropriate to the probe (and not all probes may be detected) thereby determining that the SCCmec cassette DNA is present and that it is integrated into the chromosomal DNA of *Staphylococcus aureus*. The hybridizations (a) and (b) can be carried out at the same time or can be carried out in either order. Optionally, the sample to be tested can be hybridized to one or more blocker probe(s) that hybridize to DNA of one or more other species of staphylococci as part of step (a).

Another method tests a sample for the presence of DNA of *S. aureus* comprising SCCmec. The method includes performing an amplification reaction using the sample as a source of template DNA. A first primer comprises a nucleobase sequence complementary to a nucleobase sequence within SCCmec of at least one SCCmec type of *Staphylococcus* species. A second primer hybridizes to chromosomal DNA of *S. aureus* external to SCCmec. The results of the amplification reaction are analyzed for the presence of amplification product. If the amplification product is present, DNA of *S. aureus* comprising SCCmec is present in the sample.

Further aspects of the invention are kits with components to carry out the assay methods. The kits include oligonucleotide or oligonucleotide mimics to be used as probes or primers, as appropriate to the method, and can include other reagents and solutions. A solid support may be supplied with capture probe attached, or for attachment of capture probes, for example.

DETAILED DESCRIPTION OF THE INVENTION

The design of *S. aureus*-specific probes near the integration site for the SCCmec cassette is complicated by the high degree of sequence similarity between the chromosomal DNA of *Staphylococcus* species, (herein, the term "chromosomal DNA" is limited to regions external to any SCCmec, if present) which may explain false-positive results by current methods (Francois, et al., J Clin Microbiol. 45(6):2011-2013, 2007). With this invention, improved specificity is possible using blocker probes that prevent hybridization of *S. aureus*-specific probes to other *Staphylococcus* species.

Another parameter complicating probe design is sequence heterogeneity of chromosomal DNA between *S. aureus* strains within the *S. aureus*-specific target regions, such that a single probe does not hybridize to all *S. aureus* strains as shown in Example 3. This may be overcome by simply designing multiple probes as also shown in Example 3, but this invention offers the advantage of designing fewer probes, or even a single probe directed towards a non-*S. aureus*-specific region which, when used in conjunction with blocker probes as shown in Example 6, eliminates hybridization to other *Staphylococcus* species.

The invention includes oligonucleotides and oligonucleotide mimics, including those comprising the nucleobase sequences described herein, and including those consisting of the nucleobase sequences described herein. Probes and primers comprising oligonucleotides or oligonucleotide mimics are part of the invention and are suitable for the assays described herein. Oligonucleotide mimics include, for example, phosphorothioate oligonucleotides, peptide nucleic acids (PNAs), and locked nucleic acids (LNAs). Oligonucleotide mimic portions and oligonucleotide portions (comprising at least one monomer unit, for example) can be combined in one chimeric oligonucleotide (e.g., a PNA/DNA chimera or a LNA/DNA chimera). Such chimeric oligonucleotides are also included within "oligonucleotide mimics." Like oligonucleotides that may be found naturally occurring in cells, oligonucleotide mimics are spoken of as having a nucleobase sequence according to the A, C, G, T and U base portion of each of their respective monomer units. Also like oligonucleotides that may be found naturally occurring in cells, oligonucleotide mimics can form hybrids through Watson-Crick basepairing with DNA and/or RNA comprising a nucleobase sequence that is at least partially complementary. The oligonucleotides may be isolated. An oligonucleotide or oligonucleotide mimic can be provided as (in solution for example) the only probe, or it can be provided as a combination of one or more probes.

Generic probes are presented which bind to conserved regions of nucleic acid targets, though with some mismatched bases. As described herein, probes were designed that can form hybrids with these regions even though many of the bases in the probe are mismatched. The probe design is based on an "average" sequence from the alignment of several sequences derived from nature. The probe incorporates bases at each position which are complimentary to at least one of the natural sequences. The resulting probe is partially complimentary to all of the sequences it was designed against. The design method is similar to the well known concept of degenerate probes (primers), where a given probe sequence is designed with "wobble" bases incorporated, such that the final probe produced is actually composed of a population of two or more distinct sequences based on a general core sequence. This design method is different from degenerate probes in that there is only one probe sequence based on consensus complementarities. This type of generic mismatching probe is referred to as a "consensus" probe herein.

Consensus probes can be used in combination with blocker probes. Blocker probes are well defined in the art and at their simplest can be defined as probes which bind specifically to nucleic acid targets which are not targets of interest. Very often blocker probes are designed such that they can not be detected. Blocker probes are used as part of a probe cocktail to prevent evolution of detectable signal from targets which are not of interest. Blocker probes and consensus probes together, as described herein, can be used to prevent signal evolution from specific nucleic acid targets.

The combination of blocker probes and consensus probes (with either partially or complete complementarity to the target and/or non target sequence) offers the advantage of utilizing sequence differences outside the target/non-target region, such that only a part of the blocker probe(s) is used to reduce binding of the consensus probe to the non-target sequence. The use of one and two blocker probes utilizing sequence differences is exemplified in Example 5 and 6. This aspect of the invention is not limited to the sample or assay type but is a general concept providing improved specificity for nucleic acid analysis, and can be viewed as a means of using a longer target sequence.

Another aspect of this invention is the use of very short probes which facilitates design of probes outside target regions with sequence heterogeneity. Use of very short probes, i.e. less than 10 bases, is common in the art for applications where specificity is not desired, i.e., random priming of PCR reactions with hexamers, as any given 9-mer is statistically predicted to occur every 4 to the $9^{th}$ ($4^9$=262144) bases. Very short probes are therefore not perceived by prior art in nucleic acid detection methods where high specificity is required, and in fact were specifically ruled out by earlier practitioners as being untenable for detection of SCCmec cassettes in S. aureus (US 2005019893). This exclusion may have been due to the reliance on PCR as a dominant method of nucleic acid analysis. As shown herein, very short probes containing LNA and/or PNA allow for nucleic acid detection methods, which can not be performed using conventional DNA probes of equivalent length (see Examples 4 and 5). The advantages of using short probes are not limited to the sample or assay type.

This invention is exemplified for the detection of MRSA but is equally suitable for detection of MRCNS and in fact offers the potential for using the same probe set(s) comprising consensus probe(s) and probe(s) for SCCmec for detection of the SCCmec cassette in staphylococci (with differentiation between MRSA and MRCNS (methicillin-resistant coagulase negative)) and supplemented with either blocking probes preventing hybridization of the consensus probe to non-S. aureus staphylococci for detection of MRSA, or blocking probes preventing hybridization of the consensus probe to S. aureus for detection of MRCNS.

In one embodiment, the invention comprises probes for the detection of SCCmec in S. aureus; see Examples 1, 2 and 3. Preferably, the probes comprise less than 15 nucleobases and are oligonucleotide mimics comprising LNA or PNA, detecting one or more SCCmec types (see Examples 4 and 5) and may be used in combination to detect multiple SCCmec types (see Example 4 and Example 5).

In another embodiment, the invention comprises a method for detecting SCCmec in S. aureus using the probes in combination with one or more probes hybridizing to chromosomal DNA of S. aureus. These may be either hybridizing specifically to S. aureus only (Example 6) or to other species of Staphylococci (Example 7). To eliminate hybridization to other Staphylococcus species, blocker probes may be included to prevent hybridization of the probe(s) to other Staphylococcus species (Examples 7 and 8). Steps of methods for specific purposes are described herein, wherein step a) (hybridizing the sample to one or more capture probes and step b) (hybridizing the sample to one or more detector probes) can occur by combining the appropriate reagents in sequence, or can occur by combining the appropriate reagents in one hybridization mixture so that hybridizing steps a) and b) occur at the same time.

The method to detect SCCmec in S. aureus in a sample may include lysing the cells in the sample, denaturing the DNA in the sample, incubating the DNA with one or more capture probes hybridizing to SCCmec types and one or more probes hybridizing to S. aureus chromosomal DNA. Protocols to carry out sandwich-type DNA hybridization assays or target amplification assays are known in the art.

Kits comprising probe set(s) and optionally also comprising reagents are also a part of the invention. Instructions to use the kit can also be a component of the kit. DNA control standards can also be included. Capture probes can be supplied attached to a support, such as in the wells of a microtiter plate. One capture probe can be supplied in a set of wells, or more than one capture probe can be supplied together in the same wells. Detector probes can be provided individually packaged, or more than one detector probe can be packaged together. Blocker probes, if included in the kit, can be provided individually packaged, or more than one blocker probe can be packaged together. Blocker probes can be included with detector probes. It will be understood that while certain probes that hybridize to a first region of DNA are designated herein as "capture" probes and certain probes that hybridize to a second region of DNA are designated herein as "detector" probes, probes of the sequences of capture probes can be used in assays as detector probes and vice versa, so long as the appropriate probes are used together in the assay.

This invention is exemplified using sandwich hybridization but is also applicable to other hybridization methods and to nucleic acid amplification techniques.

DNA amplification methods (e.g., polymerase chain reaction) can be used to detect MRSA in a sample, as these methods, in effect, detect a nucleobase sequence internal to SCCmec, and a nucleobase sequence on the S. aureus chromosome external to SCCmec on a template DNA of S. aureus present in the sample. The amplification methods can use as primers any of the oligonucleotides or oligonucleotide mimics described as probes herein, or can use shorter portions of those molecules. Primers of a variety of lengths, comprising PNA or LNA, can be used, e.g., primers of 14, 13, 12 11, 10 or fewer monomers. The primers can comprise the nucleobase sequences described for any of the oligonucleotides or oligonucleotide mimics described herein as capture probes or detector probes, so that a primer pair for amplification consists of one oligonucleotide or oligonucleotide mimic with the nucleobase sequence of a capture probe and one oligonucleotide or oligonucleotide mimic with the nucleobase sequence of a detector probe.

It should be noted from the results in Example 12 that LNA/DNA primers (comprising both LNA and DNA monomers) shorter than DNA primers of the same sequence can be used successfully to amplify DNA by the polymerase chain reaction. LNA/DNA primers as short as 10 monomer units resulted in amplified product.

The detection of MRSA by sandwich hybridization methods and by amplification methods such as the methods shown herein exemplifies a more general method that can be applied to the detection of other DNA or RNA targets (e.g., a gene for virulence in pathogenic bacteria, an allele associated with a genetic disease in humans, or a sequence indicating a mutation, a chromosomal rearrangement, deletion or insertion). The use of short LNA or LNA/DNA oligonucleotide mimics as probes or primers as demonstrated herein (see, for example, Examples 11 and 12) can be generally applied to the detection of other target DNAs in other assays. Oligonucleotide mimics comprising LNA can be substituted for oligonucleotides of the same nucleobase sequence for use as primers or probes, with greater sensitivity in assays. The length of an effective probe or primer can be shorter in an oligonucleotide mimic comprising LNA, compared to an oligonucleotide.

As used herein, the word "hybridize" or "hybridizing" means the sequence specific binding of any of two single stranded nucleic acids or oligonucleotides or oligonucleotide mimics to form duplexes according to Watson-Crick base-pairing rules. Hybrids may form between two nucleobase sequences which are not perfectly complementary as defined by the W-C base pairing rules, but are substantially complimentary such that they form stable double stranded complexes under assay conditions, also referred to as partially complementary consensus probes.

A sample to be used in the assays described herein can be, for example, bacteria from one or more isolated colonies, or bacteria grown in a liquid or other culture, either isolated or mixed. Additionally, a sample can be bodily fluid or washings as might be obtained for analysis in a clinical laboratory, or an aliquot of such fluid or washings.

*Staphylococcus* species is used to indicate any of the species of staphyloccoci.

EXAMPLES

Materials and Methods

The examples below use EVIGENE, a sandwich-type DNA hybridization assay (Skov et al., Journal of Antimicrobial Chemotherapy 43: 467-475, 1999; Levi and Towner, J. Clin. Microbiol. 38: 830-838, 2003) to specifically detect genetic markers in staphylococci. EVIGENE kit components (AdvanDx, Woburn, Mass.) and generic assay products were used for all experiments differing only by the individual probes as listed in the Examples below. For each sample, 2 drops of Lysis I solution were added to 2 mL microcentrifuge tubes with lockable lids. Using a 1 µL plastic inoculating loop, 2 loops of colonies were collected and transferred to the tube and vortexed until the bacteria were completely suspended. The tube was incubated in a heating block or water bath at 35-37° C. for 20 min. Two drops of Lysis II solution were added to the tube and vortexed thoroughly. The tube was incubated in a heating block at 95-100° C. for 15 min, vortexed and incubated at 95-100° C. for another 15 min. The tubes were allowed to cool at room temperature for 5 min. One drop of Detector Probes was added into a well in a microtiter well with immobilized Capture Probes followed by 100 µL of the sample (lysed bacteria) from the tube. The resulting mixture comprised NaCl, Tris and detergent as known to facilitate hybridization of the probes to the bacterial nucleic acid. The well was covered with plate sealing tape and placed in a microtiter plate shaker/incubator set at 55° C. and 400 rpm and incubated for 60 min. After incubation, the well was emptied and 2 drops of Conjugate Buffer were added, followed by 1 drop of Conjugate. The well was covered with plate sealing tape and incubated at 35-37° C. for 30 min. After the end of incubation, the well was then emptied, washed 4 times with 7 drops (or 4×200 µl) of Wash Solution. One drop of Substrate A was added followed by 2 drops of Substrate B and the solution was incubated at room temperature for 30 min. Two drops of Stop Solution were added and absorbance was measured at 492 nm using an ELISA plate reader. Other assay formats, including PCR or other target amplification techniques, may also be used with the probe sets.

A variety of bacteria strains from AdvanDx A/S, Denmark were used. The identity (species and type, if available) of each isolate was based on information available from the supplier of the strains and/or other tests, such as EVIGENE tests for detection of mecA (gene for methicillin resistance) and nuc (*S. aureus*-specific gene).

DNA probes and probes comprising LNA nucleobases were obtained from TAG Copenhagen A/S (Copenhagen, Denmark). Capture probes were labeled for immobilization onto microtiter wells and Detector probes were labeled for detection via colorimetric signal amplification using components from commercial EVIGENE kits (AdvanDx). Blocker probes were unlabeled.

Example 1

Detection of SCCmec Type I, II, and IV in *S. aureus*, Only

Table 1.1 displays the nucleobase sequences of the Capture and Detector probes used in the experiment. The Capture probe targets the *S. aureus* DNA and has 10 mismatches to *Staphylococcus epidermidis* DNA. The Detector probe targets SCCmec types I, II, and IV (not III and V).

TABLE 1.1

Nucleobase Sequences

| Probe Type | Name | Sequence (5' to 3') |
|---|---|---|
| Capture | GenCP2 | AATCCTTCGGAAGATAGCATCTTTCCTTGTATTTCT AATG (SEQ ID NO: 1) |
| Detector | Dt1 | GCTATTATTTACTTGAAATGAAAGACTGCGGAGGCT AACT (SEQ ID NO: 2) |

Method

Samples were prepared and assayed essentially according to the EVIGENE™ procedure using Capture probe GenCP2 (60 nM) and Detector Probe Dt1 (5 nM).

Results

The mecA result of each isolate (using the MRSA EVIGENE™ kits) as well as the MRSA results according to the invention, i.e. specific detection of mecA in *S. aureus* by detection of the SCCmec cassette in *S. aureus* only, are shown in Table 1.2. The final column displays the absorbance readings at 492 nm. Absorbance readings above background levels indicate the presence of the nucleic acid target in the sample.

TABLE 1.2

Results of Example 1

| Species | ATCC# | Type | MecA | MRSA | OD 492 |
|---|---|---|---|---|---|
| *Staphylococcus aureus* | 6538 | MecA neg. | Negative | Negative | 0.287 |
| *Stphylococcus epidermis* | 51625 | CNS | Positive | Negative | 0.153 |
| *Enterococcus faecalis* | 51299 | | Negative | Negative | 0.122 |
| *Enterococcus faecium* | 700221 | | Negative | Negative | 0.116 |
| *Staphylococcus aureus* | | SCCmec type I | Positive | Positive | 1.231 |
| *Staphylococcus aureus* | | SCCmec type Ia | Positive | Positive | 1.049 |
| *Staphylococcus aureus* | | SCCmec type II | Positive | Positive | 1.121 |
| *Staphylococcus aureus* | | SCC mec type II | Positive | Negative | 0.185 |
| *Staphylococcus aureus* | | SCCmec type IIa | Positive | Negative | 0.215 |
| *Staphylococcus aureus* | | SCCmec type IV | Positive | Positive | 1.033 |
| *Staphylococcus aureus* | | SCCmec type IV - PV_pos. ST80 | Positive | Positive | 1.261 |
| *Staphylococcus epidermis* | | CNS | Positive | Negative | 0.171 |
| Unknown | | CNS | Positive | Negative | 0.165 |
| *Staphylococcus haemolyticus* | | CNS | Positive | Negative | 0.244 |
| *Staphylococcus simulans* | 27851 | CNS | Negative | Negative | 0.167 |
| *Staphylococcus warneri* | 49454 | CNS | Negative | Negative | 0.178 |
| *Staphylococcus aureus* | | | Negative | Negative | 0.135 |
| *Staphylococcus aureus* | | | Negative | Negative | 0.139 |
| *Staphylococcus fleurettii* | BAA-274 | CNS | Positive | Negative | 0.436 |
| *Staphylococcus* | | | Positive | Negative | 0.205 |
| *Staphylococcus saccharolyticus* | 14953 | CNS | Positive | Negative | 0.192 |
| *Staphylococcus aureus* | 700699 | MecA pos. | Positive | Positive | 0.673 |
| *Staphylococcus aureus* | | MecA pos. | Positive | Positive | 0.974 |
| *Staphylococcus aureus* | | MecA pos. | Negative | Negative | 0.140 |
| *Escherichia coli* | 35218 | | Negative | Negative | 0.184 |
| *Candida krusei* | Y-7550 | | Negative | Negative | 0.120 |
| *Staphylococcus aureus* | | SCCmec type I | Positive | Positive | 1.628 |
| *Staphylococcus aureus* | | SCCmec type Ia | Positive | Positive | 1.328 |
| *Staphylococcus aureus* | | SCCmec type I | Positive | Positive | 1.297 |
| *Staphylococcus aureus* | | SCCmec IA - MecA pos. | Positive | Positive | 0.614 |
| *Staphylococcus aureus* | | SCCmec type II | Positive | Positive | 1.315 |
| *Staphylococcus aureus* | | SCCmec type II | Positive | Positive | 1.204 |
| *Staphylococcus aureus* | | SCCmec type II | Positive | Positive | 1.402 |
| *Staphylococcus aureus* | | SCCmec type IIIa | Positive | Negative | 0.211 |
| *Staphylococcus aureus* | | SCCmec type IIIa | Positive | Negative | 0.142 |
| *Staphylococcus aureus* | | SCCmec type III | Positive | Negative | 0.133 |
| *Staphylococcus aureus* | | SCCmec type IV | Positive | Positive | 1.324 |
| *Staphylococcus aureus* | | SCCmec type III | Positive | Negative | 0.172 |
| *Staphylococcus aureus* | | SCC mec type V | Positive | Negative | 0.141 |
| *Staphylococcus aureus* | | SCCmec type IV | Positive | Positive | 1.306 |
| *Staphylococcus aureus* | | Spa type 10$$5 | Positive | Positive | 1.300 |
| *Staphylococcus aureus* | | Spa type 1044 | Positive | Positive | 1.345 |
| *Staphylococcus aureus* | | Spa type 1175 | Positive | Positive | 1.021 |
| *Staphylococcus aureus* | | Spa type 1019 | Positive | Positive | 1.420 |
| Unknown | SSI B | CNS - MecA/nuc pos. | Positive | Negative | 0.230 |

The results clearly show that only mecA-positive *S. aureus* strains of SCCmec type I, II or IV tested positive ($OD_{492}$>0.5); whereas, mecA-positive staphylococci other than *S. aureus*, mecA-negative *S. aureus* and other bacterial and yeast strains all tested negative ($OD_{492}$<0.5). The results also showed that mecA-positive *S. aureus* strains of SCCmec type III and V tested negative, as the Detector probe was not designed for these SCCmec types.

The data also show that sandwich hybridization, such as EVIGENE, is a suitable assay format and is thus an alternative to PCR for specific detection of SCCmec in *S. aureus*.

Example 2

Detection of SCCmec Type I, II, III, IV and V in Only *S. Aureus*

Table 2.1 displays the nucleobase sequences of the Capture and Detector probes used in the experiment. Capture probe GenCP2 (the same as in Example 1). Detector probe Dt1 (designed to be specific for SCCmec type I, II & IV), Detector probe Type III (designed to be specific for SCCmec type III) and Detector probe Type V (designed to specific for SCCmec type V, Table 2.1).

TABLE 2.1

Nucleobase Sequences

| Probe Type | Name | Sequence (5' to 3') |
|---|---|---|
| Capture | GenCP2 | AATCCTTCGGAAGATAGCATCTTTCCTTGTATTT CTAATG (SEQ ID NO: 1) |
| Detector | Dt1 | GCTATTATTTACTTGAAATGAAAGACTGCGGAGG CTAACT (SEQ ID NO: 2) |
| Detector | Type III | TAATCCAATATTTCATATATGTAATTCCTCCACA TCTCAT SEQ ID NO: 3) |
| Detector | Type V | ACTTTAGTCAAATCATCTTCACTAGTGTAATTAT CGAATG (SEQ ID NO: 4) |

Method

Samples were prepared and assayed essentially according to the EVIGENE™ procedure using Capture probe GenCP2 (60 nM) and Detector Probe Dt1 (5 nM). Detector Probe Type III (5 nM), or Detector Probe Type V (5 nM).

TABLE 2.2

Results of Example 2
Capture probe GenCp2

| Species | AdvanDx ID | Type | Dt1 (Type I, II, IV) | OD 492 | Type III | OD 492 | Type V | OD 492 |
|---|---|---|---|---|---|---|---|---|
| *Staphylococcus aureus* | #294 | SCCmec type I | Positive | 1.628 | Negative | 0.179 | Negative | 0.194 |
| *Staphylococcus aureus* | #296 | SCCmec type I | Positive | 1.297 | Negative | 0.166 | Negative | 0.174 |
| *Staphylococcus aureus* | #295 | SCCmec type Ia | Positive | 1.328 | Negative | 0.192 | Negative | 0.185 |
| *Staphylococcus aureus* | #298 | SCCmec type II | Positive | 1.316 | Negative | 0.186 | Negative | 0.204 |
| *Staphylococcus aureus* | #299 | SCCmec type II | Positive | 1.204 | Negative | 0.203 | Negative | 0.178 |
| *Staphylococcus aureus* | #300 | SCCmec type II | Positive | 1.402 | Negative | 0.172 | Negative | 0.157 |
| *Staphylococcus aureus* | #301 | SCCmec type IIIa | Negative | 0.211 | Positive | 1.255 | Negative | 0.178 |
| *Staphylococcus aureus* | #303 | SCCmec type III | Negative | 0.133 | Positive | 1.297 | Negative | 0.198 |
| *Staphylococcus aureus* | #305 | SCCmec type III | Negative | 0.172 | Positive | 1.280 | Negative | 0.202 |
| *Staphylococcus aureus* | #304 | SCCmec type IV | Positive | 1.324 | Negative | 0.158 | Negative | 0.171 |
| *Staphylococcus aureus* | #307 | SCCmec type IV - PVL pos. | Positive | 1.306 | Negative | 0.216 | Negative | 0.351 |
| *Staphylococcus aureus* | #460 | Type V | Negative | 0.250 | Negative | 0.232 | Positive | 1.091 |
| *Staphylococcus warneri* | #351 | MR-CNS | Negative | 0.160 | Negative | 0.139 | Negative | 0.224 |
| *Staphylococcus epidermis* | #352 | MR-CNS | Negative | 0.166 | Negative | 0.164 | Negative | 0.330 |
| *Staphylococcus hominis* | #353 | MR-CNS | Negative | 0.185 | Negative | 0.142 | Positive | 0.578 |

Results

The results show that only MRSA strains typed as SCCmec type I, II & IV tested positive ($OD_{492}>0.5$) with Detector Dt1 and strains typed as SCCmec type III tested positive ($OD_{492}>0.5$) with Detector Type III and strains typed as SCCmec type V tested positive ($OD_{492}>0.5$) with Detector Type V; whereas, mecA-positive staphylococci other than *S. aureus*, all tested negative ($OD_{492}<0.5$).

Example 3

Table 3.1 displays the nucleobase sequences of the Capture and Detector probes used in the experiment. Additional detector probes were tested based on sequences in WO02099034. Two Capture probes GenCP2 (used in previous Examples) and GenCP3 were tested with Detector probes Dt1, Type III, Type V, Type5 (specific for SCCmec type V, WO02099034), Type4 (specific for SCCmec type IV, WO02099034), Type7 (specific for SCCmec type VII, WO02099034), type 6 (specific for SCCmec type VI, WO02099034), or type 8,9 (designed to be specific for SCCmec types VIII and IX, WO02099034).

TABLE 3.1

Nucleobase Sequences

| Probe Type | Name | Sequence (5' to 3') |
|---|---|---|
| Capture | GenCP2 | AATCCTTCGGAAGATAGCATCTTTCCTTGTATT TCTAATG (SEQ ID NO: 1) |
| Capture | GenCP3 | TGTTCAATTAACACAACCCGCATCATTTGATGT GGGAATG (SEQ ID NO: 5) |
| Detector | Dt1 | GCTATTATTTACTTGAAATGAAAGACTGCGGAG GCTAACT (SEQ ID NO: 2) |
| Detector | Type III | TAATCCAATATTTCATATATGTAATTCCTCCAC ATCTCAT (SEQ ID NO: 3) |

TABLE 3.1-continued

Nucleobase Sequences

| Probe Type | Name | Sequence (5' to 3') |
|---|---|---|
| Detector | Type V | ACTTTAGTCAAATCATCTTCACTAGTGTAATTA TCGAATG (SEQ ID NO: 4) |
| Detector | Type5 | TAATAAACTCTGCTTTATATTATAAAATTACGG CTGAAATAACC (SEQ ID NO: 6) |
| Detector | Type4 | TGTTTTCTTCAAATATTATCTCGTAATTTACCT TGTTCATTAAAC (SEQ ID NO: 7) |
| Detector | Type7 | TTTATTCTTCAAAGATTTGAGCTAATTTAATAA TTTTCTCATA (SEQ ID NO: 8) |
| Detector | type 6 | AATTAATCTGATTTTCACTCTTCATCTACTTAC TCATATT (SEQ ID NO: 9) |
| Detector | type 8, 9 | AACATAACAGCAATTCACATAAACCTCATATGT TCTGATA (SEQ ID NO: 10) |

Method

Samples were prepared and assayed essentially according to the EVIGENE™ procedure using Capture probe GenCP2 (60 nM) and Detector probe Dt1 (5 nM) and Detector probe Type III (5 nM), or Detector probe Type V (5 nM), Detector probe Type5 (5 nM), Detector probe Type4 (5 nM), Detector probe Type7 (5 nM), Detector probe type 6 (5 nM), or Detector probe type 8,9 (5 nM). The Capture probe GenCP3 was tested together with Detector probe Dt1, Type III, and Type V (5 nM each) or with Detector probe Type5 (5 nM), Detector probe Type4 (5 nM), Detector probe Type7 (5 nM), Detector probe type 6 (5 nM), or Detector probe type 8,9 (5 nM).

TABLE 3.2

Results of Example 3

Capture probe GenCp2

| Sample | ID | Dt1 & Type III | OD 492 | Type V | OD 492 | Type 5 | OD 492 | Type 4 | OD 492 | Type 7 | OD 492 | Type 6 | OD 492 | Type 8, 9 | OD 492 |
|---|---|---|---|---|---|---|---|---|---|---|---|---|---|---|---|
| Clinical isolate | #360 | Negative | 0.155 | Negative | 0.115 | Negative | 0.264 | Negative | 0.216 | Negative | 0.185 | Negative | 0.214 | Positive | 1.672 |
| Clinical isolate | #361 | Negative | 0.159 | Negative | 0.124 | Negative | 0.290 | Negative | 0.226 | Negative | 0.267 | Negative | 0.201 | Positive | 1.769 |
| Clinical isolate | #389 | Negative | 0.121 | Negative | 0.111 | Negative | 0.226 | Positive | 1.578 | Negative | 0.205 | Negative | 0.153 | Negative | 0.172 |
| Clinical isolate | #391 | Negative | 0.135 | Negative | 0.124 | Positive | 1.947 | Negative | 0.236 | Negative | 0.251 | Negative | 0.204 | Negative | 0.179 |
| Clinical isolate | #395 | Negative | 0.141 | Negative |  | Negative | 0.212 | Negative | 0.183 | Positive | 1.711 | Negative | 0.146 | Negative | 0.243 |
| Clinical isolate | #396 | Negative | 0.129 | Negative | 0.116 | Positive | 1.703 | Negative | 0.218 | Negative | 0.223 | Negative | 0.195 | Negative | 0.226 |
| Clinical isolate | #397 | Negative | 0.136 | Negative | 0.109 | Negative | 0.229 | Negative | 0.230 | Negative | 0.273 | Negative | 0.185 | Negative | 0.239 |

Capture probe GenCp3

| Sample | ID | Dt1 & Type III & Type V | OD 492 | Type 5 | OD 492 | Type 4 | OD 492 | Type 7 | OD 492 | Type 6 | OD 492 | Type 8, 9 | OD 492 |
|---|---|---|---|---|---|---|---|---|---|---|---|---|---|
| Clinical isolate | #397 | Negative | 0.130 | Negative | 0.124 | Negative | 0.105 | Negative | 0.119 | Positive | 1.840 | Negative | 0.105 |

Results

The results in Example 3 show that the strains which did not test positive with GenCp2 and the detector probes described in Example 2 (Dt1, Type III & Type V) tested positive when alternate detector probes or another capture probe (GenCp3) was included in the test. The data show that multiple Capture and Detector probes may improve sensitivity and that additional probes may be added as additional "false-negative" strains (new SCCmec types) occur.

Example 4

Detection of mecA in Only *S. aureus* by Detection of the SCCmec Cassette in *S. aureus* with 9-mer LNA Probe Table 4.1 displays the nucleobase sequences of the Capture and Detector probes used in the experiment.

TABLE 4.1

Nucleobase Sequences

| Probe Type | Name | Sequence (5' to 3') |
|---|---|---|
| Capture | GenCP3 | TGTTCAATTAACACAACCCGCATCATTTG ATGTGGGAATG (SEQ ID NO: 5) |
| Detector | Dt1 | GCTATTATTTACTTGAAATGAAAGACTGC GGAGGCTAACT (SEQ ID NO: 2) |
| Detector T1, 2, 4- | Dt5 | GaggctaaC (SEQ ID NO: 11) |
| Detector T1, 2, 4- | Dt8 | GAGGCTAAC (SEQ ID NO: 12) |

LNA monomers are lowercase a, g, c, t, and DNA monomers are uppercase A, G, C, T Method Samples were prepared and assayed essentially according to the EVIGENE™ procedure using the Detector probe Dt1 (5 nM), 9-mer Dt5 LNA/DNA (50 nM) or 9-mer DNA (50 nM) and Capture probe GenCp3 (60 nM) above (Table 4.1).

Results

Results of Example 4 are summarized in Table 4.2, which displays the absorbance values obtained at 492 nm and the positive/negative results for the samples. The experiment showed that only the methicillin-resistant *S. aureus* strains of SCCmec type I, II or IV were positive ($OD_{492}$>0.5) using the Capture GenCp3 and a 40-mer DNA or a LNA/DNA 9-mer Detector Probe, whereas a 9-mer DNA Detector Probe with the same sequence as the LNA/DNA gave a negative result when testing the same samples.

The data also show that replacing some of the naturally occurring nucleotides with non-naturally-occurring LNA monomers allows for use of short probes.

Example 5

Detection of mecA in Only *S. aureus* by Detection of the SCCmec Cassette in *S. aureus* with 9-mer PNA Probe Table 5.1 displays the nucleobase sequences of the Capture and Detector probes used in the experiment. The 9-mer PNA Detector Probe Dt10 was designed to detect SCCmec type I, II and IV.

TABLE 5.1

Nucleobase Sequences

| Probe Type | Name | Sequence (5' to 3') |
|---|---|---|
| Capture | GenCP2 | AATCCTTCGGAAGATAGCATCTTTCCTTGTAT TTCTAATG (SEQ ID NO: 1) |
| Detector T1, 2, 4- | Dt 10 | ctgcggagg (SEQ ID NO: 13) |

PNA monomers are lowercase a, g, c, t, and DNA monomers are uppercase A, G, C, T Method Samples were prepared and assayed essentially according to the EVIGENE™ procedure using the Detector probe 9-mer Dt10 PNA (50 nM) and Capture probe GenCp2 (60 nM) above (Table 5.1).

TABLE 4.2

Results of Example 4

| Species | ADx ID | Type | Dt1 (Type I, II, IV) | OD 492 | Dt5 (Type I, II, IV) 9-mer LNA/DNA | OD 492 | Dt8 (Type I, II, IV) 9-mer DNA | OD 492 |
|---|---|---|---|---|---|---|---|---|
| Staphylococcus aureus | #294 | SCCmec type I | Positive | 2.475 | Positive | 1.713 | Negative | 0.123 |
| Staphylococcus aureus | #295 | SCCmec type Ia | Positive | 2.398 | Negative | 0.469 | Negative | 0.112 |
| Staphylococcus aureus | #298 | SCCmec type II | Positive | 2.766 | Positive | 1.992 | Negative | 0.164 |
| Staphylococcus aureus | #303 | SCCmec type III | Negative | 0.112 | Negative | 0.111 | Negative | 0.118 |
| Staphylococcus aureus | #301 | SCCmec type IIIa | Negative | 0.118 | Negative | 0.095 | Negative | 0.138 |
| Staphylococcus aureus | #304 | SCCmec type IV | Positive | 2.981 | Positive | 1.584 | Negative | 0.125 |
| Staphylococcus aureus | #307 | SCCmec type IV + PVL | Positive | 2.783 | Positive | 1.694 | Negative | 0.121 |
| Staphylococcus aureus | #460 | Type V | Negative | 0.116 | Negative | 0.098 | Negative | 0.127 |
| Staphylococcus warneri | #351 | MR-CNS | Negative | 0.389 | Negative | 0.169 | Negative | 0.131 |
| Staphylococcus epidermidis | #352 | MR-CNS | Negative | 0.129 | Negative | 0.101 | Negative | 0.124 |
| Staphylococcus hominis | #353 | MR-CNS | Negative | 0.116 | Negative | 0.097 | Negative | 0.175 |
| Staphylococcus aureus | #156 | MSSA | Negative | 0.112 | Negative | 0.101 | Negative | 0.114 |

Results

TABLE 5.2

Results of Example 5

| Species | ADx ID | Type | Dt10 (Type I, II, IV) 9-mer PNA | OD 492 |
|---|---|---|---|---|
| Staphylococcus aureus | #294 | SCCmec type I | Positive | 0.659 |
| Staphylococcus aureus | #295 | SCCmec type Ia | Positive | 0.674 |
| Staphylococcus aureus | #297 | SCCmec type Ia | Positive | 0.535 |
| Staphylococcus aureus | #298 | SCCmec type II | Positive | 0.797 |
| Staphylococcus aureus | #303 | SCCmec type III | Negative | 0.230 |
| Staphylococcus aureus | #301 | SCCmec type IIIa | Negative | 0.290 |
| Staphylococcus aureus | #304 | SCCmec type IV | Positive | 0.651 |
| Staphylococcus aureus | #460 | Type V | Negative | 0.200 |
| Staphylococcus warneri | #351 | MR-CNS | Negative | 0.198 |
| Staphylococcus epidermidis | #352 | MR-CNS | Negative | 0.194 |
| Staphylococcus hominis | #353 | MR-CNS | Negative | 0.177 |
| Staphylococcus aureus | #156 | MSSA | Negative | 0.191 |

Results of Example 5 are summarized in Table 5.2, which displays the absorbance values obtained at 492 nm and the positive/negative results for the samples. The experiment showed that only the methicillin-resistant *S. aureus* strains of SCCmec type I, II or IV were positive ($OD_{492} > 0.5$) using the Capture GenCp2 and PNA 9-mer Detector Probe (Dt10). The data also show that replacing some of the naturally occurring nucleotides with non-naturally-occurring PNA monomers allows for the use of short probes.

Type5, Type4, Type7, type 6 and type 8,9, Table 3.1) and Blocker probes (B4A and B4B or the B5, Table 6.1) were used.

TABLE 6.1

Nucleobase Sequences

| Probe Type | Name | Sequence (5' to 3') |
|---|---|---|
| Capture | GenCP3 | TGTTCAATTAACACAACCCGCATCATTTGATGTGGG AATG (SEQ ID NO: 5) |
| Detector | All | See note* |
| Blocker | B4A | ATTTGGTGTGGGAAGGTCATCTTGCTGAA (SEQ ID NO: 14) |
| Blocker | B4B | TCGATATACTTGTTCTATCAACACGACGCG (SEQ ID NO: 15) |
| Blocker | B5 | TGTTCTATCAACACGACGCGCATCATTTGG TGTGGGAAGG (SEQ ID NO: 16) |

* All Dt SCCmec: Dt1, type III, type V, Type5, Type4, Type7, type 6 and type 8, 9 (see Example 3 for the sequences)

Method

Samples were prepared and assayed essentially according to the EVIGENE™ procedure using the Detector probes (5 nM each) and Capture probe GenCp3 (60 nM) above with and without the Blocker probes (50 nM each).

TABLE 6.2

Results of Example 6

| Species | ADx ID | Type | All Dt SCCmec − Blocker | OD 492 | All Dt SCCmec + Blocker B4A/B4B | OD 492 | All Dt SCCmec + Blocker B5 | OD 492 |
|---|---|---|---|---|---|---|---|---|
| Staphylococcus aureus | #294 | SCCmec type I | Positive | 2.307 | Positive | 2.346 | Positive | 2.026 |
| Staphylococcus aureus | #295 | SCCmec type Ia | Positive | 2.431 | Positive | 2.399 | Positive | 2.366 |
| Staphylococcus aureus | #298 | SCCmec type II | Positive | 2.602 | Positive | 2.638 | Positive | 2.499 |
| Staphylococcus aureus | #303 | SCCmec type III | Positive | 1.154 | Positive | 0.928 | Positive | 0.844 |
| Staphylococcus aureus | #301 | SCCmec type IIIa | Positive | 1.417 | Positive | 1.255 | Positive | 1.060 |
| Staphylococcus aureus | #304 | SCCmec type IV | Positive | 2.607 | Positive | 2.459 | Positive | 2.537 |
| Staphylococcus aureus | #307 | SCCmec type IV + PVL | Positive | 2.167 | Positive | 2.523 | Positive | 2.503 |
| Staphylococcus aureus | #460 | Type V | Positive | 1.161 | Positive | 0.998 | Positive | 0.755 |
| Staphylococcus warneri | #351 | MR-CNS | Positive | 1.377 | Negative | 0.165 | Negative | 0.161 |
| Staphylococcus epidermidis | #352 | MR-CNS | Negative | 0.129 | Negative | 0.101 | Negative | 0.124 |
| Staphylococcus hominis | #353 | MR-CNS | Negative | 0.113 | Negative | 0.112 | Negative | 0.146 |
| Staphylococcus aureus | #156 | MSSA | Negative | 0.313 | Negative | 0.263 | Negative | 0.207 |

Example 6

Specific Detection of MRSA with *S. warneri* Blocker Probes

Table 6.1 displays the nucleobase sequences of the Capture and Detector probes used in the experiment.

In the experiment below, Capture probe (GenCp3, Table 4.1), all the SCCmec Detector probes (Dt1, type III, type V, Results Results of Example 6 are summarized in Table 6.2, which displays the absorbance values obtained at 492 nm and the positive/negative results for the samples. The cut off value is set at $OD_{492 \text{ or } 490} = 0.500$. Signals greater than or equal to the cut-off value are considered positive. Signals less than cut-off value are considered negative. Using the Capture (GenCp3) and all the SCCmec Detector Probes, all methicillin-resistant *S. aureus* strains (all SCCmec types) were positive as well as methicillin-resistant *S. warneri*.

By using Blocker probes designed to hybridize to chromosomal DNA of *S. warneri* (not *S. aureus*), specific detection of methicillin-resistant *S. aureus* was obtained.

The Blocker probes thus effectively prevent the Capture probe from hybridizing to chromosomal DNA of *S. warneri*, thereby allowing for specific detection of methicillin-resistant *S. aureus*.

Example 7

Use of Blocker Probes for Specific Detection of MRSA Using a Consensus Capture Probe Table 7.1 displays the nucleobase sequences of the Capture (GenCp4) and Detector probe (Dt) and Blocker probes (B1A and B1B) used in the experiment below. The Capture probe is designed to hybridize to chromosomal DNA of *S. aureus* and *S. epidermidis*. The Detector probe is designed to hybridize to SCCmec type I, II & IV (not III and V) and the Blocker probes are designed to hybridize to chromosomal DNA of *S. epidermidis* (not *S. aureus*).

TABLE 7.1

| Probe Type | Name | Sequence (5' to 3') |
|---|---|---|
| Capture | GenCP4 | CAAATACAAAGTCGCTTTGCCCTTGTGTCA (SEQ ID NO: 17) |
| Detector | Dt1 | GCTATTATTTACTTGAAATGAAAGACTGCGGAGGCTAACT (SEQ ID NO: 2) |
| Blocker | B1A | TTTGACCTTGTGTCATGCGTGTTTGTAGTTCTTTAGCGAG (SEQ ID NO: 18) |
| Blocker | B1B | TGTAAACCATTGGAGCCACCTATGACAAATGTAAAGTCGC (SEQ ID NO: 19) |

Method

Samples were prepared and assayed essentially according to the EVIGENE™ procedure using the Detector (5 nM) and Capture probes (60 nM) above with and without the Blocker probes (50 nM each).

Results

Results of Example 7 are summarized in Table 7.2, which displays the absorbance values obtained at 492 nm and the positive/negative results for the samples. Absorbance readings ($OD_{492}$>0.5) above background levels indicate the presence of the nucleic acid target in the sample.

TABLE 7.2

Results of Example 7

| Species | AdvanDx ID | Type | Dt1 (Type I, II, IV) − Blocker | OD 492 | Dt1 (Type I, II, IV) + Blocker B1A/B1B | OD 492 |
|---|---|---|---|---|---|---|
| *Staphylococcus aureus* | #9 | SCCmec type I | Positive | 1.965 | Positive | 1.796 |
| *Staphylococcus aureus* | #10 | SCCmec type Ia | Positive | 1.884 | Positive | 2.201 |
| *Staphylococcus aureus* | #11 | SCCmec type II | Positive | 1.854 | Positive | 1.800 |
| *Staphylococcus aureus* | #12 | SCCmec type III | Negative | 0.114 | Negative | 0.123 |
| *Staphylococcus aureus* | #13 | SCCmec type IIIa | Negative | 0.098 | Negative | 0.107 |
| *Staphylococcus aureus* | #14 | SCCmec type IV | Positive | 2.371 | Positive | 1.839 |
| *Staphylococcus aureus* | #460 | Type V | Negative | 0.114 | Negative | 0.100 |
| *Staphylococcus epidermidis* | #355 | MR-CNS | Positive | 1.310 | Negative | 0.114 |
| *Staphylococcus aureus* | #156 | MSSA | Negative | 0.143 | Negative | 0.124 |

The methicillin-resistant *S. epidermidis* and methicillin-resistant *S. aureus* strains of SCCmec type I, II or IV were all positive ($OD_{492}$>0.5) using the Capture and Detector Probe, whereas only the methicillin-resistant *S. aureus* strains were positive when using Blocker probes. The Blocker probes thus effectively prevent the Capture probe from hybridizing to chromosomal DNA of *S. epidermidis*, thereby allowing for specific detection of methicillin-resistant *S. aureus* without using a *S. aureus*-specific capture probe. This aspect of the invention provides an advantage over previous design schemes as the location of the probe is less limited.

Example 8

MRSA Detection with a Consensus Capture Probe, Blocker Probes and 9-mer LNA Detector Probe Table 8.1 displays the nucleobase sequences of the Capture (GenCp4) and the Blocker probes (B1A and B1B) from Example 7, combined with the Detector probe (Dt5) from Example 4.

TABLE 8.1

Nucleobase Sequences

| Probe Type | Name | Sequence (5' to 3') |
|---|---|---|
| Capture | GenCP4 | CAAATACAAAGTCGCTTTGCCCTTGTGTCA (SEQ ID NO: 17) |
| Detector | T1, 2, 4-Dt5 | GaggctaaC (SEQ ID NO: 11) |
| Blocker | B1A | TTTGACCTTGTGTCATGCGTGTTTGTAGTTCTTTAGCGAG (SEQ ID NO: 18) |
| Blocker | B1B | TGTAAACCATTGGAGCCACCTATGACAAATGTAAAGTCGC (SEQ ID NO: 19) |

LNA monomers are lowercase a, g, c, t, and DNA monomers are uppercase A, G, C, T Method Samples were prepared and assayed essentially according to the EVIGENE™ procedure using the Detector (Dt5, 50 nM) and Capture probe (GenCp4, 60 nM) above with and without the Blocker probes (B1A and B1B, 500 nM each).

Results

TABLE 8.2

Results of Example 8

| Species | AdvanDx ID | Type | Dt5 (Type I, II, IV) – Blocker | OD 492 | Dt5 (Type I, II, IV) + Blocker B1A/B1B | OD 492 |
|---|---|---|---|---|---|---|
| Staphylococcus aureus | #9 | SCCmec type I | Positive | 1.030 | Positive | 0.771 |
| Staphylococcus aureus | #10 | SCCmec type Ia | Positive | 1.168 | Positive | 0.967 |
| Staphylococcus aureus | #11 | SCCmec type II | Positive | 1.206 | Positive | 0.955 |
| Staphylococcus aureus | #12 | SCCmec type III | Negative | 0.130 | Negative | 0.157 |
| Staphylococcus aureus | #13 | SCCmec type IIIa | Negative | 0.112 | Negative | 0.124 |
| Staphylococcus aureus | #14 | SCCmec type IV | Positive | 1.106 | Positive | 1.130 |
| Staphylococcus aureus | #460 | Type V | Negative | 0.122 | Negative | 0.129 |
| Staphylococcus epidermidis | #355 | MR-CNS | Positive | 0.561 | Negative | 0.155 |
| Staphylococcus aureus | #156 | MSSA | Negative | 0.124 | Negative | 0.223 |

Results of Example 8 are summarized in Table 8.2, which displays the absorbance values obtained at 492 nm and the positive/negative results for the samples. Absorbance readings ($OD_{492}>0.5$) above background levels indicate the presence of the nucleic acid target in the sample. This example shows that the Blocker probes prevent the Capture probe from hybridizing to chromosomal DNA of *S. epidermidis*, thereby allowing for specific detection of methicillin-resistant *S. aureus* without using a *S. aureus*-specific capture probe. The results also showed that mecA-positive *S. aureus* strains of SCCmec type I, II or IV tested positive with a 9-mer Detector probe hybridized together with the *S. epidermidis* Blocker probes.

Example 9

Detection of SCCmec Types I, II & IV Using 9-mer LNA/DNA or 9-mer LNA Probe

Table 9.1 displays the nucleobase sequences of the Capture probe GenCp3 with the Detector probe Dt5 (from Examples 4 and 8), Dt12 and Dt1.

TABLE 9.1

| Probe Type | Name | Sequence (5' to 3') |
|---|---|---|
| Capture | GenCP3 | TGTTCAATTAACACAACCCGCATCATTTG ATGTGGGAATG (SEQ ID NO: 5) |
| Detector | Dt1 | GCTATTATTTACTTGAAATGAAAGACTGC GGAGGCTAACT (SEQ ID NO: 2) |
| Detector | T1, 2, 4-Dt5 | GaggctaaC (SEQ ID NO: 11) |
| Detector | T1, 2, 4-Dt12 | gaggctaac (SEQ ID NO: 20) |

LNA monomers are lowercase a, g, c, t, and DNA monomers are uppercase A, G, C, T Method Samples were prepared and assayed essentially according to the EVIGENE™ procedure using the Detector probe Dt1 (5 nM), 9-mer Dt5 LNA (50 nM) or 9-mer LNA (50 nM) with Capture probe GenCp3 (60 nM) above (Table 9.1).

Results

Results of Example 9 are summarized in Table 9.2, which displays the absorbance values obtained at 492 nm and the positive/negative results for the samples. The experiment showed that the methicillin-resistant *S. aureus* strains of SCCmec type I, II or IV were positive ($OD_{492}>0.5$) using the Capture GenCp3 with a 40-mer DNA or 9-mer mixed LNA/DNA Dt5 or a 9-mer only LNA (Dt12) Detector Probe.

The data also show that replacing some or all of the naturally occurring DNA nucleotides with non-naturally-occurring LNA monomers allows for use of short probes.

TABLE 9.2

Results of Example 9

| Species | | OD 492 | Dt5 (Type I, II, IV) | OD 492 | Dt12 (Type I, II, IV) | OD 492 | Dt1 (Type I, II, IV) | OD 492 |
|---|---|---|---|---|---|---|---|---|
| *Staphylococcus aureus* | #295 | SCCmec type Ia | Positive | 1.547 | Positive | 1.832 | Positive | 2.218 |
| *Staphylococcus aureus* | #298 | SCCmec type II | Positive | 1.616 | Positive | 1.944 | Positive | 2.075 |
| *Staphylococcus aureus* | #16 | SCCmec type IV | Positive | 1.644 | Positive | 1.906 | Positive | 1.783 |
| *Staphylococcus aureus* | #156 | MSSA | Negative | 0.144 | Negative | 0.168 | Negative | 0.200 |

Example 10

Detection of SCCmec Type III Detection with 9-mer LNA/DNA Probe

Table 10.1 displays the nucleobase sequences of the Capture probe (GenCp3) and the Detector probes Type III and Type III-Dt2.

TABLE 10.1

| Probe Type | Name | Sequence (5' to 3') |
|---|---|---|
| | Nucleobase Sequences | |
| Capture | GenCP3 | TGTTCAATTAACACAACCCGCATCATTTG ATGTGGGAATG (SEQ ID NO: 5) |
| Detector | Type III | TAATCCAATATTTCATATATGTAATTCCT CCACATCTCAT (SEQ ID NO: 3) |
| Detector | Type III-Dt2 | TtcctccaC (SEQ ID NO: 21) |

LNA monomers are lowercase a, g, c, t, and DNA monomers are uppercase A, G, C, T

Method

Samples were prepared and assayed essentially according to the EVIGENE™ procedure using the Detector probe Type III (5 nM) and 9-mer Type III-Dt2 LNA/DNA probe (50 nM) and Capture probe GenCp3 (60 nM) above (Table 10.1).

TABLE 10.2

| Species | ADx ID | Type | Type III-Dt2 | OD 492 | Type III | OD 492 |
|---|---|---|---|---|---|---|
| | | Results of Example 10 | | | | |
| Staphylococcus aureus | #303 | SCCmec type III | Positive | 1.732 | Positive | 1.693 |
| Staphylococcus aureus | #301 | SCCmec type IIIa | Positive | 1.676 | Positive | 1.704 |
| Staphylococcus epidermidis | #352 | MR-CNS | Negative | 0.214 | Negative | 0.117 |
| Staphylococcus aureus | #156 | MSSA | Negative | 0.273 | Negative | 0.158 |

Results of Example 10 are summarized in Table 10.2, which displays the absorbance values obtained at 492 nm and the positive/negative results for the samples. The experiment showed that the methicillin-resistant *S. aureus* strains of SCCmec type III were positive ($OD_{492} > 0.5$) using Capture probe GenCp3 and a 40-mer DNA or 9-mer mixed LNA/DNA Detector Probe.

Example 11

Detection of SCCmec Type V Using 9-mer LNA Probe

Table 11.1 displays the nucleobase sequences of the Capture (GenCp3) with the Detector probes Type V and Type V-Dt4.

TABLE 11.1

| Probe Type | Name | Sequence (5' to 3') |
|---|---|---|
| | Nucleobase Sequences | |
| Capture | GenCP3 | TGTTCAATTAACACAACCCGCATCATTTGATGTG GGAATG (SEQ ID NO: 5) |
| Detector | Type V | ACTTTAGTCAAATCATCTTCACTAGTGTAATTAT CGAATG (SEQ ID NO: 4) |
| Detector | Type V-Dt4 | accattcac (SEQ ID NO: 22) |

LNA monomers are lowercase a, g, c, t, and DNA monomers are uppercase A, G, C, T Method Samples were prepared and assayed essentially according to the EVIGENE™ procedure using the Detector probe Type V (5 nM) and 9-mer Type V-Dt4 LNA probe (50 nM) and Capture probe GenCp3 (60 nM) above (Table 10.1).

TABLE 11.2

Results of Example 11

| Species | Type | Type V-Dt4 | OD 492 | Type V | OD 492 |
|---|---|---|---|---|---|
| Staphylococcus aureus | SCCmec type V | Positive | 0.647 | Positive | 0.588 |
| Staphylococcus aureus | MSSA | Negative | 0.155 | Negative | 0.113 |

Results of Example 11 are summarized in Table 11.2, which displays the absorbance values obtained at 492 nm and the positive/negative results for the samples. The experiment showed that the methicillin-resistant *S. aureus* strain of SCCmec type V was positive ($OD_{492} > 0.5$) using the Capture GenCp3 and a 40-mer DNA or 9-mer LNA only Detector Probe. MSSA is methicillin sensitive *Staphylococcus aureus*.

Example 12

Use of Short LNA PCR Primers for Specific Detection of MRSA

Table 12.1 displays the nucleobase sequences of the PCR primers with specific LNA substitutions used in the PCR experiment below. The primers are designed to hybridize to genomic DNA of *S. aureus* or to a SCCmec type II as found in *S. aureus* strain Mu50.

TABLE 12.1

Nucleobase Sequences

| Primer | Name | Sequence (5' to 3') |
|---|---|---|
| FORWARD | | |
| Dt1 | F1 | GCTATTATTTACTTGAAATGAAAGACTGCGGAGGCTAACT (SEQ ID NO: 2) |
| Dt1 | F5 | GcGgAgGCTAACT (SEQ ID NO: 23) |
| Dt1 | F5-DNA | GCGGAGGCTAACT (SEQ ID NO: 24) |
| Dt1 | F7 | AcTGcGGaGGCTAACT (SEQ ID NO: 25) |
| Dt1 | F8 | cTGcGGaGGCTAAC (SEQ ID NO: 26) |
| Dt1 | F15 | cgGaGGCTAAC (SEQ ID NO: 27) |
| Dt1 | F15-DNA | CGGAGGCTAAC (SEQ ID NO: 28) |
| Dt1 | F16 | cgGaGGCTAA (SEQ ID NO: 29) |
| Dt1 | F16-DNA | CGGAGGCTAA (SEQ ID NO: 30) |
| REVERSE | | |
| GenCP2 | R1 | CATTAGAAATACAAGGAAAGATGCTATCTTCCGAAGGATT (SEQ ID NO: 31) |
| GenCP3 | R1 | CATTCCCACATCAAATGATGCGGGTTG (SEQ ID NO: 32) |
| GenCP3 | R3 | ggGtTgTGTTAATT (SEQ ID NO: 33) |
| GenCP3 | R3-DNA | GGGTTGTGTTAATT (SEQ ID NO: 34) |
| GenCP3 | R7 | ggGtTgTGTTAA (SEQ ID NO: 35) |
| GenCP3 | R7-DNA | GGGTTGTGTTAA (SEQ ID NO: 36) |

LNA monomers are lowercase a, g, c, t, and DNA monomers are uppercase A, G, C, T Method The DNA template was genomic bacterial DNA (Mu50, ATCC 700699), isolated with DNeasy Blood & Tissue kit (Qiagen). All DNA and LNA primers were suspended in 10 mM Tris. PCR amplification was performed in 50 μL reactions using 1 of each PCR primer, 800 ng or 8 ng genomic DNA and AccuPrime Taq DNA polymerase with AccuPrime buffer II, and 10 mM dNTPs (Invitrogen). Thermal cycling began with denaturation at 94.0° C. for 3 min followed by 30 cycles of 94.0° C. for 30 s, 55.0° C. for 30 s and 68.0° C. for 30 s. PCR product was visualized on 2% agarose gels with ethidium bromide and a 100 bp DNA ladder (Invitrogen). Images of the gels were taken with a digital camera.

TABLE 12.2

| Gel A | | | Gel B | | |
|---|---|---|---|---|---|
| Lane | Sample | Conc. | Lane | Sample | Conc. |
| 2 | 100 bp DNA ladder | 0.5 μg | 2 | 100 bp DNA ladder | 0.5 μg |
| 3 | Cp2-R1 + Dt1-F5 | Undil. | 3 | Cp3-R1 + Dt1-F5 | Undil. |
| 4 | Cp2-R1 + Dt1-F5 | 1:100 | 4 | Cp3-R1 + Dt1-F5 | 1:100 |
| 5 | Cp2-R1 + Dt1-F7 | Undil. | 5 | Cp3-R1 + Dt1-F7 | Undil. |
| 6 | Cp2-R1 + Dt1-F7 | 1:100 | 6 | Cp3-R1 + Dt1-F7 | 1:100 |
| 7 | Cp2-R1 + Dt1-F8 | Undil. | 7 | Cp3-R1 + Dt1-F8 | Undil. |
| 8 | Cp2-R1 + Dt1-F8 | 1:100 | 8 | Cp3-R1 + Dt1-F8 | 1:100 |
| 9 | Cp2-R1 + Dt1-F1 | Undil. | 9 | Cp3-R1 + Dt1-F1 | Undil. |
| 10 | Cp2-R1 + Dt1-F1 | 1:100 | 10 | Cp3-R1 + Dt1-F1 | 1:100 |
| 11 | 100 bp DNA ladder | 0.5 μg | 11 | 100 bp DNA ladder | 0.5 μg |

Forward and reverse primer sequences are listed in Table 12.1. The forward Dt-F1 (SEQ ID NO:2) primer has the same sequence as Detector probe Dt1 used in the previous experiments. The primer pairs are listed in Table 12.2. Eight different primer pairs were tested for amplification of 800 ng (undiluted) or 8 ng (1:100) genomic DNA. All lanes of the agarose gels that were loaded with an aliquot of the completed amplification reaction showed a strong band of DNA of the expected length on 400 by (Gel A: forward primer: Dt-F1, -F5, -F7 or F8 paired with GenCp2-R1 reverse primer) and 200 by (Gel B: forward primer: Dt-F1, -F5, -F7 or F8 paired with GenCp3-R1 reverse primer).

TABLE 12.3

| Lane | Sample | | Band |
|---|---|---|---|
| Gel C | | | |
| 14-mer + 13-mer | | | |
| 1 | 100bp DNA ladder | | |
| 2 | Cp3-R3 + Dt1-F5 | LNA-LNA | 200 bp |
| 3 | Cp3-R3 + Dt1-F5-DNA | LNA-DNA | 200 bp |
| 4 | Cp3-R3-DNA + Dt1-F5 | DNA-LNA | None |
| 5 | Cp3-R3-DNA + Dt1-F5-DNA | DNA-DNA | None |
| 12-mer + 13-mer | | | |
| 6 | Cp3-R7 + Dt1-F5-DNA | | 200 bp |
| 7 | Cp3-R7-DNA + Dt1-F5 | LNA-DNA | 200 bp |
| 8 | Cp3-R7-DNA + Dt1-F5-DNA | DNA-LNA | None |
| 9 | Cp3-R7-DNA + Dt1-F5-DNA | DNA-DNA | None |
| 10 | 100 bp DNA ladder | | |
| Gel D | | | |
| 14-mer + 11-mer | | | |
| 4 | 100bp DNA ladder | | |
| 5 | Cp3-R3 + Dt1-F15 | LNA-LNA | 200 bp |
| 6 | Cp3-R3 + Dt1-F15-DNA | LNA-DNA | Faint 200 bp |
| 7 | Cp3-R3-DNA + Dt1-F15 | DNA-LNA | None |

TABLE 12.3-continued

| Lane | Sample | | Band |
|---|---|---|---|
| 8 | Cp3-R3-DNA + Dt1-F15-DNA | DNA-DNA | None |
| 9 | 100 bp DNA ladder | | |
| Gel E | | | |
| 14-mer + 10-mer | | | |
| 1 | 100bp DNA ladder | | |
| 2 | Cp3-R3 + Dt1-F16 | LNA-LNA | Faint 200 bp |
| 3 | Cp3-R3 + Dt1-F16-DNA | LNA-DNA | None |
| 4 | Cp3-R3-DNA + Dt1-F16 | DNA-LNA | None |
| 5 | Cp3-R3-DNA + Dt1-F16-DNA | DNA-DNA | None |
| 6 | 100 bp DNA ladder | | |

Forward and reverse primer sequences are listed in Table 12.1. The primer pairs are listed in Table 12.3. In Gel C, eight different primer pairs were tested for amplification of 800 ng (undiluted) DNA. All amplicons (200 bp) were made with a forward Dt1-F5 (13-mer LNA/DNA primer) or Dt-F5-DNA (13-mer DNA primer), paired with GenCP3-R3 (14-mer LNA/DNA primer) or GenCP3-R7 (12-mer LNA/DNA) as reverse primers. In Gel D, four different primer pairs were tested for amplification of 800 ng (undiluted) DNA (Gel D, Table 12.3). All amplicons (200 bp) were made with a forward Dt1-F15 (11-mer LNA/DNA) primer or Dt-F11-DNA (11-mer DNA) primer, and GenCP3-R3 (14-mer LNA/DNA), reverse primer. In Gel E, four different primer pairs were tested for amplification of 800 ng (undiluted) DNA (Gel D, Table 12.3). All amplicons (200 bp) were made with a forward Dt1-F16 (10-mer LNA/DNA) primer or Dt-F16-DNA (10-mer DNA) primer, and GenCP3-R3 (14-mer LNA/DNA) reverse primer.

In Gel C, lanes 2 and 3 had strong bands of DNA of the expected length as a product of the amplification reaction. Lanes 6 and 7 had fainter bands. Other primer combinations did not result in detectable product.

In Gel D, lane 2 had strong band and lane 3 had faint band of DNA of the expected length of amplification product. See Table 12.3 for the primer combinations. Other primer combinations did not result in detectable product.

In Gel E, lanes 2 had faint band of DNA of the expected length of amplification product. See Table 12.3 for the primer combinations. Other primer combinations did not result in detectable product.

The PCR experiments showed that LNA incorporation improves the efficiency of short, low-$T_m$, (AT-rich) primers. Three or four LNA subunits were incorporated into each primer, because this was sufficient to elevate the predicted melting temperatures into the range that resulted in products visible on stained agarose gels as good bands. Previous work showed that PCR failed when primers had more than three LNAs (Ugozzoli, L. A. et al., Anal. Biochem 324:143-152, 2004) but the results on Gels B, C, D and E demonstrated that a 14-mer, or 12-mer primer containing 4 LNA monomers successfully primed amplification.

The experiment showed that the methicillin-resistant S. aureus strain Mu50 of SCCmec type II was detected by PCR by using a 13-, 11- or a 10-mer forward LNA/DNA and a 14- or a 12-mer reverse LNA/DNA primer, but not detected by PCR when using DNA-only primers with the same sequence and length.

What is claimed is:

1. A method of testing a sample for the presence or absence of SCCmec cassette DNA in DNA of *Staphylococcus aureus*, the method comprising:
   a) hybridizing the sample to one or more capture probes that hybridize to DNA of *Staphylococcus aureus* and one or more other species of staphylococci external to SCCmec cassette DNA, the capture probes optionally attached to a support;
   b) hybridizing the sample to one or more blocker probes that hybridize to DNA of one or more other species of staphylococci;
   c) hybridizing the sample to one or more detector probes that hybridize to SCCmec cassette DNA; and
   d) detecting or not detecting each of the detector probes, thereby determining the presence or absence, respectively, of the SCCmec cassette DNA in the DNA of the *Staphylococcus aureus*,
   wherein the one or more capture probes include a capture probe that comprises SEQ ID NO:5; wherein the one or more detector probes include a detector probe comprising SEQ ID NO:2, SEQ ID NO:3, SEQ ID NO:4, SEQ ID NO:6, SEQ ID NO:7, SEQ ID NO:8, SEQ ID NO:9, SEQ ID NO:10, SEQ ID NO:11, SEQ ID NO:20, SEQ ID NO:21 or SEQ ID NO:22; and wherein the one or more blocker probes include a blocker probe comprising SEQ ID NO:14, SEQ ID NO:15 or SEQ ID NO:16.

2. A method of testing a sample for the presence or absence of SCCmec cassette DNA in DNA of a plurality of *Staphylococcus* species, the method comprising:
   a) hybridizing the sample to one or more capture probes that hybridize to DNA of a plurality of *Staphylococcus* species external to SCCmec cassette DNA, the capture probes optionally attached to a support;
   b) hybridizing the sample to one or more blocker probes that hybridize to the DNA of one or more of the plurality of *Staphylococcus* species;
   c) hybridizing the sample to one or more detector probes that hybridize to SCCmec cassette DNA; and
   d) detecting or not detecting each of the detector probes, thereby determining the presence or absence, respectively, of the SCCmec cassette DNA in the DNA of the plurality of *Staphylococcus* species;
   wherein the one or more capture probes include a capture probe that comprises SEQ ID NO:5; wherein the one or more detector probes include a detector probe comprising SEQ ID NO:2, SEQ ID NO:3, SEQ ID NO:4, SEQ ID NO:6, SEQ ID NO:7, SEQ ID NO:8, SEQ ID NO:9, SEQ ID NO:10, SEQ ID NO:11, SEQ ID NO:20, SEQ ID NO:21 or SEQ ID NO:22; and wherein the one or more blocker probes include a blocker probe comprising SEQ ID NO:14, SEQ ID NO:15 or SEQ ID NO:16.

3. A method of testing a sample for the presence or absence of SCCmec cassette DNA in DNA of *Staphylococcus aureus*, the method comprising:
   a) hybridizing the sample to a capture probe that comprises SEQ ID NO:5, wherein the capture probe is optionally attached to a support;
   b) hybridizing the sample to two or more blocker probes that hybridize to DNA of one or more other species of staphylococci, wherein the two or more blocker probes include a blocker probe comprising SEQ ID NO:14 and a blocker probe comprising SEQ ID NO:15;
   c) hybridizing the sample to one or more detector probes that hybridize to SCCmec cassette DNA; and
   d) detecting or not detecting each of the detector probes, thereby determining the presence or absence, respectively, of the SCCmec cassette DNA in the DNA of the *Staphylococcus aureus*.

* * * * *

UNITED STATES PATENT AND TRADEMARK OFFICE
CERTIFICATE OF CORRECTION

PATENT NO.        : 8,206,921 B2
APPLICATION NO.   : 12/620187
DATED             : June 26, 2012
INVENTOR(S)       : Henrik Stender, Anne Rasmussen and Mark J. Fiandaca It is certified that error appears in the above-identified patent and that said Letters Patent is hereby corrected as shown below:

In Column 41, Claim 1, delete lines 12-35 and insert:
--a) hybridizing the sample to a capture probe comprising SEQ ID NO:5, wherein the capture probe is optionally attached to a support;
b) hybridizing the sample to one or more blocker probes that hybridize to DNA of one or more other species of staphylococci, wherein the blocker probes are selected from the group consisting of SEQ ID NO:14, SEQ ID NO:15, and SEQ ID NO:16;
c) contacting the sample under conditions that permit hybridization to one or more detector probes that hybridize to SCC*mec* cassette DNA, wherein the detector probes are selected from the group consisting of SEQ ID NO:2, SEQ ID NO:3, SEQ ID NO:4, SEQ ID NO:6, SEQ ID NO:7, SEQ ID NO:8, SEQ ID NO:9, SEQ ID NO:10, SEQ ID NO:11, SEQ ID NO:20, SEQ ID NO:21 and SEQ ID NO:22; and
d) detecting or not detecting the one or more detector probes, thereby determining the presence or absence, respectively, of the SCC*mec* cassette DNA in the DNA of the *Staphylococcus aureus*.--

In Column 41, Claim 2, delete lines 39-42 continuing all the way through Column 42, line 24 and insert:
--a) hybridizing the sample to a capture probe comprising SEQ ID NO:5, wherein the capture probe is optionally attached to a support;
b) hybridizing the sample to one or more blocker probes that hybridize to the DNA of one or more of the plurality of *Staphylococcus* species, wherein the blocker probes are selected from the group consisting of SEQ ID NO:14, SEQ ID NO:15, and SEQ ID NO:16;
c) contacting the sample under conditions that permit hybridization to one or more detector probes that hybridize to SCC*mec* cassette DNA, wherein the detector probes are selected from the group consisting of SEQ ID NO:2, SEQ ID NO:3, SEQ ID NO:4, SEQ ID NO:6, SEQ ID NO:7, SEQ ID NO:8, SEQ ID NO:9, SEQ ID NO:10, SEQ ID NO:11, SEQ ID NO:20, SEQ ID NO:21 and SEQ ID NO:22; and
d) detecting or not detecting each of the detector probes, thereby determining the presence or absence, respectively, of the SCC*mec* cassette DNA in the DNA of the plurality of *Staphylococcus* species.--

Signed and Sealed this
Twenty-eighth Day of August, 2012

David J. Kappos
*Director of the United States Patent and Trademark Office*

In Column 42 Claim 3, delete lines 36-37 and insert:
--c) contacting the sample under conditions that permit hybridization to one or more detector probes that hybridize to SCC*mec* cassette DNA; and--